(12) United States Patent
Yonehara et al.

(10) Patent No.: US 7,820,404 B2
(45) Date of Patent: Oct. 26, 2010

(54) PROTEIN CLEAVAGE METHOD AND USE THEREOF

(75) Inventors: Satoshi Yonehara, Kyoto (JP); Norio Inamura, Kyoto (JP)

(73) Assignee: Arkray, Inc., Kyoto (JP)

(*) Notice: Subject to any disclaimer, the term of this patent is extended or adjusted under 35 U.S.C. 154(b) by 206 days.

(21) Appl. No.: 11/919,791

(22) PCT Filed: May 2, 2006

(86) PCT No.: PCT/JP2006/309164

§ 371 (c)(1),
(2), (4) Date: Nov. 2, 2007

(87) PCT Pub. No.: WO2006/120976

PCT Pub. Date: Nov. 16, 2006

(65) Prior Publication Data

US 2009/0081718 A1 Mar. 26, 2009

(30) Foreign Application Priority Data

May 6, 2005 (JP) .............................. 2005-135298

(51) Int. Cl.
*C12Q 1/37* (2006.01)
(52) U.S. Cl. ....................................................... 435/23
(58) Field of Classification Search ........................ None
See application file for complete search history.

(56) References Cited

U.S. PATENT DOCUMENTS

| | | | |
|---|---|---|---|
| 5,370,990 | A | 12/1994 | Staniford et al. |
| 5,712,138 | A | 1/1998 | Kato et al. |
| 5,789,221 | A | 8/1998 | Kato et al. |
| 5,824,527 | A | 10/1998 | Kato et al. |
| 5,948,659 | A | 9/1999 | Kato et al. |
| 6,033,867 | A | 3/2000 | Kato et al. |
| 6,797,503 | B1 | 9/2004 | Ishimaru et al. |
| 6,825,016 | B1 | 11/2004 | Ishimaru et al. |
| 7,070,948 | B1 | 7/2006 | Sakaue et al. |
| 2003/0162242 | A1 | 8/2003 | Yonehara |
| 2003/0186346 | A1 | 10/2003 | Yagi et al. |
| 2003/0186449 | A1 | 10/2003 | Yonehara et al. |
| 2005/0042709 | A1 | 2/2005 | Yonehara et al. |
| 2005/0059613 | A1 | 3/2005 | Memarzadeh et al. |
| 2006/0172367 | A1 | 8/2006 | Yoshida et al. |

FOREIGN PATENT DOCUMENTS

| | | |
|---|---|---|
| EP | 1 362 925 | 11/2003 |
| JP | 5-192193 | 8/1993 |
| JP | 7-289253 | 11/1995 |
| JP | 8-154672 | 6/1996 |
| JP | 8-336386 | 12/1996 |
| JP | 10-33177 | 2/1998 |
| JP | 10-33180 | 2/1998 |
| JP | 2000-300294 | 10/2000 |
| JP | 2001-57897 | 3/2001 |
| JP | 2001-95598 | 4/2001 |
| JP | 2002-315600 | 10/2002 |
| JP | 2004-275013 | 10/2004 |
| JP | 2004-275063 | 10/2004 |
| JP | 2004-333452 | 11/2004 |
| JP | 2004-344052 | 12/2004 |
| WO | 97/13872 | 4/1997 |
| WO | 99/20039 | 4/1999 |
| WO | 00/50579 | 8/2000 |
| WO | 00/61732 | 10/2000 |
| WO | 02/06519 | 1/2002 |
| WO | 02/27012 | 4/2002 |
| WO | 02/27330 | 4/2002 |
| WO | 03/062461 | 7/2003 |
| WO | 03/064683 | 8/2003 |
| WO | 2004/029251 | 4/2004 |

OTHER PUBLICATIONS

Sakurabayashi et al. "New enzymatic assay for glycohemoglobin", Clinical Chemistry, 2003, 49(2):269-274.*

Sakaue et al. "Cloning and expression of fructosyl-amino acid oxidase gene from Corynebacterium sp. 2-4-1 in *E. coli*", Biosci. Biotechnol. Biochem. 2002, 66(6):1256-1261.*

Umemoto, "IFCC Method of HbA1c for International Standardization", Clinical examination, vol. 46, No. 7, Jul. 2002.

Fujiwara, et al., "Conversion of Substrate Specificity of Amino Acid Oxidase Derived from Fusarium oxysporum", Annual Meeting 2000, The Society for Biotechnology, Japan, with its partial English translation.

Katayama, et al., "Efficient in-gel digestion procedure using 5-cyclohexyl-1-pentyl-β-D-maltoside as an additive for gel-based membrane proteomics", Rapid Communications in Mass Spectrometry, 2004; 18: 2388-2394.

* cited by examiner

*Primary Examiner*—Jon P Weber
*Assistant Examiner*—Bin Shen
(74) *Attorney, Agent, or Firm*—Hamre, Schumann, Mueller & Larson, P.C.

(57) ABSTRACT

The present invention provides a method for cleaving a glycated protein to obtain an amino acid or a peptide efficiently with a protease. By treating the glycated protein with the protease in the presence of a compound represented by R—X, the amino acid or the peptide is obtained by the cleavage. The R represents an alkyl compound with a carbon number of 9 or more, and preferably is straight-chain alkyl or straight-chain acyl with a carbon number of 9 to 16, branched-chain alkyl or branched-chain acyl with a carbon number of 10 to 40 and a main-chain carbon number of 9 to 16, or straight-chain alkyl that is substituted by cycloalkyl (a carbon number of the cycloalkyl ranges from 3 to 8, and a carbon number of the straight chain ranges from 4 to 13), where X is a sugar residue. Moreover, the glycated protein is, for example, glycated hemoglobin, and preferably β-chain N-terminal amino acid or a β-chain N-terminal peptide is cleaved by the protease treatment.

17 Claims, 2 Drawing Sheets

```
                       SEQUENCE LISTING

<160> NUMBER OF SEQ ID NOS: 1

<210> SEQ ID NO 1
<211> LENGTH: 4
<212> TYPE: PRT
<213> ORGANISM: human
<220> FEATURE:
<221> NAME/KEY: CARBOHYD
<222> LOCATION: (1)..(1)
<223> OTHER INFORMATION: valine is glycated to form fructosyl valine

<400> SEQUENCE: 1

Val His Leu Thr
1
```

PROTEIN CLEAVAGE METHOD AND USE THEREOF

TECHNICAL FIELD

The present invention relates to a protein cleavage method and a method for assaying a protein glycation degree using the same.

BACKGROUND ART

As an indicator for showing a biological state, the glycation degrees of various kinds of proteins are assayed. Among them, a glycation degree of hemoglobin (Hb) in a blood cell, in particular, HbA1c is used as an important indicator in diagnoses, treatments and the like for diabetes, because the HbA1c reflects histories of an in-vivo blood glucose level. The HbA1c has a structure in which a glucose binds to a β-chain N-terminal amino acid (valine) of HbA ($\alpha_2\beta_2$), and its glycation degree (%) is represented by a ratio (%) of a HbA1c amount with respect to a total Hb amount.

In general, HbA1c is assayed by a high performance liquid chromatography (HPLC), an immunization method, an enzymatic method, an electrophoresis or the like. For example, a method, which includes cleaving a β-chain N-terminal Hexpep of Hb and a glycated Hexpep as its glycated product by a protease Glu-C, separating and refining by the HPLC, and subsequently determining a quantity thereof by capillary electrophoresis or LC-MS, is disclosed as a reference method of HbA1c (Non-patent Document 1). Among them, the enzymatic method is, for example, an assay method as described below. Firstly, a fructosyl amino acid oxidase (hereinafter, referred to as a "FAOD") is allowed to act on a glycated part of Hb, thereby generating hydrogen peroxide. An amount of this hydrogen peroxide corresponds to an amount of the glycated Hb. Then, a peroxidase (hereinafter, referred to as a "POD") and a chromogenic substrate that develops color by oxidation are added further to this reaction liquid, so that a redox reaction occurs between the hydrogen peroxide and the chromogenic substrate with the POD as a catalyst. Then, a glycation amount is obtained by assaying a chromogenic level of the chromogenic substrate, and as a result, a HbA1c value (%) can be calculated from the glycation amount and the total Hb amount.

As described above, since the HbA1c is characterized in the glycation of the β-chain N-terminal valine, the FAOD is desired to act on the N-terminal glycated valine efficiently. However, since the FAOD is not likely to act directly on a protein, a method of cleaving the β-chain N-terminal of the Hb by protease treatment and allowing the FAOD to act on the β-chain N-terminal directly is attempted generally. More specifically, methods of using an endo-type or exo-type protease (Patent Document 1), serine carboxypeptidase (Patent Document 2), a protease that liberates amino acid whose α-amino group is glycated (Patent Documents 3 to 5), a protease that cleaves glycated amino acid or a glycated peptide at a β-chain N-terminal by a stronger action than that at an α-chain N-terminal (Patent Document 6) and the like are reported (Patent Documents 7 to 10). Moreover, a method of denaturating hemoglobin by boiling with urea added, and treating with a protease also is reported.

However, according to these methods, a long period of time is required for the protease treatment, so that it is difficult to carry out the examination swiftly. It is reported that, also in the above-described capillary electrophoresis and the protease treatment for the LC-MS, the treatment at 37° C. for 18 hours is required. Moreover, an example of carrying out the treatment with molsin under an acid condition at pH of 3 for about 1 hour is disclosed (Patent Document 11) as an example of reducing the time of the protease treatment, but substantial neutrality is preferable for effecting the enzyme reaction, and the treatment under such a condition is not disclosed. Also in the case of assaying a glycation degree of a part of the Hb other than the β-chain N-terminal, there is a problem in the speed of the cleavage, similarly to the case of the HbA1c described above.

Non-patent Document 1: Masao UMEMOTO, "IFCC Method of HbA1c for International Standardization", Clinical examination, Vol. 46, No. 7, July 2002

| | |
|---|---|
| Patent Document 1: | WO 1997/013872 A1 |
| Patent Document 2: | JP 2001-57897 A |
| Patent Document 3: | WO 2000/50579 A1 |
| Patent Document 4: | WO 2000/61732 A1 |
| Patent Document 5: | JP 2002-315600 A |
| Patent Document 6: | JP 2004-344052 A |
| Patent Document 7: | JP 5(1993)-192193 A |
| Patent Document 8: | JP 10(1998)-33177 A |
| Patent Document 9: | JP 10(1998)-33180 A |
| Patent Document 10: | JP 2004-333452 A |
| Patent Document 11: | JP 2001-95598 A |

DISCLOSURE OF INVENTION

Problem to be Solved by the Invention

In the light of the problems described above, it is an object of the present invention to provide a method for cleaving a protein to obtain amino acid or a peptide by a protease efficiently, a method for assaying a glycation degree of the protein using the same, and an accelerating agent to be used in the same.

Means for Solving Problem

The present invention provides a method for cleaving a protein to obtain an amino acid or a peptide by a protease, wherein the protein is subjected to protease treatment in the presence of a compound represented by Formula (I) below. In the below formula, R represents an alkyl group or a substituted alkyl group with a carbon number of 9 or more, and X represents a sugar residue.

R—X  (1)

Moreover, the present invention provides a method for assaying a protein glycation degree including: a step of cleaving a protein by a protease; a step of allowing a FAOD to act on a glycated part of the obtained protein cleavage product; and a step of measuring a redox reaction between the glycated part and the FAOD so as to determine the protein glycation degree, wherein the protein is cleaved by the protein cleavage method of the present invention, and the FAOD is allowed to act on a glycated part of an amino acid or a peptide obtained thereby.

Further, the accelerating agent of the present invention is an accelerating agent for accelerating cleavage of a protein to obtain an amino acid or a peptide by a protease, including a compound represented by the above Formula (I).

Effects of the Invention

According to the protein cleavage method of the present invention, although a mechanism thereof is not known, an amino acid or a peptide can be obtained by the cleavage in a short period of time, by treating a protein by a protease in the presence of the compound represented by the above Formula (I) (hereinafter, also referred to as an "accelerating compound"). Also, in the assay of the glycation degree, characteristic parts of the respective proteins can be cleaved more quickly than in the conventional methods. Thus, if treating a protein according to the cleavage method of the present invention, the time required for the protease treatment can be reduced, and a glycated amino acid and a glycated peptide that are characteristic to the respective glycated proteins can be cleaved efficiently, so that a FAOD is allowed to act on the characteristic glycated parts (for example, a glycated part of a β-chain N-terminal valine, a lysine or the like of Hb) easily, thereby improving the accuracy of assaying the glycation degree. Thus, the cleavage method and the method for assaying a glycation degree of the present invention are significantly useful in the medical field, such as diagnoses and treatment for diabetes, for example. Moreover, since the inventors of the present invention have found, for the first time, that the above-described compound accelerates the cleavage of glycated proteins, the accelerating agent of the present invention containing the compound represented by the above Formula (I) serves as a significantly useful reagent in the medical field as described above.

BRIEF DESCRIPTION OF DRAWINGS

FIG. 2A represents a result obtained by using a sample with a HbA1c value (%) of 44%, and FIG. 2B represents a result obtained by using a sample with the HbA1c value (%) of 0%.

DESCRIPTION OF THE INVENTION

1. Protein Cleavage Method

An accelerating compound represented by (I) to be used in the present invention will be described below.

$$R-X \qquad (I)$$

In the above Formula (I), R represents an alkyl group or a substituted alkyl group with a carbon number of 9 or more. Examples thereof include a straight-chain alkyl group or a straight-chain acyl group with a carbon number of 9 to 16, a branched-chain alkyl group or a branched-chain acyl group with a carbon number of 10 to 40 and a main-chain carbon number of 9 to 16, a straight-chain alkyl group that is substituted with cycloalkyl (for example, a carbon number of the cycloalkyl ranges from 3 to 8, and a carbon number of the straight chain except for the cycloalkyl ranges from 4 to 13) and the like. Examples of the cycloalkyl include cyclohexyl, cyclopenthyl, cyclobutyl and the like.

In the above Formula (I), X represents a sugar residue, and preferably is a residue of a monosaccharide or a disaccharide, for example. Examples of the monosaccharide include mannoside, glucoside, thioglucoside and the like, and examples of the disaccharide include maltoside, fructopyranosyl-glucopyranoside, thiomaltoside and the like. Structures of these sugars may be either of α, β, D or L. Moreover, hydrogen to be bonded to a cyclic structure of the sugar and hydrogen in an OH group may be substituted by Na, K, halogen or the like, for example. Incidentally, in the present invention, atoms via which R and the cyclic structure of the sugar residue are bonded (for example, —O—, —S— and the like) are components of the sugar residue.

Examples of the accelerating compound of the present invention include n-dodecyl-β-D-maltoside (n-dodecyl-β-D-maltopyranoside), 6-cyclohexylhexyl-β-D-maltoside, sucrose monolaurate (β-D-fructopyranosyl-α-D-glucopyranoside monododecanoate), n-decyl-β-D-maltoside (n-decyl-β-D-maltopyranoside), n-nonyl-β-D-thiomaltoside (n-nonyl-β-D-thiomaltoside), 5-cyclohexylpenthyl-β-D-maltoside, undecyl-β-D-maltoside, n-dodecyl-α-D-maltoside, hexadecyl-β-D-maltoside and 3-oxamidecyl-α-D-mannoside and the like. Chemical formulae of these compounds will be described below.

6-Cyclohexylhexyl-β-D-maltoside

Sucrose monolaurate

-continued n-Decyl-β-D-maltoside n-Dodecyl-β-D-maltoside n-Nonyl-β-D-thiomaltoside n-Hexadecyl-β-D-maltoside 5-Cyclohexylpentyl-β-D-maltoside Undecyl-β-D-maltoside 3-Oxatridecyl-α-D-mannoside Among them, n-dodecyl-β-D-maltoside, sucrose monolaurate, hexadecyl-β-D-maltoside and the like, whose carbon number of R (alkyl chain) in the above Formula (I) are 12 or more, are preferable. Moreover, in the case where the carbon numbers of R are the same (for example, the alkyl group and the acyl group that are the same in carbon number), the acyl group is more preferable, so that n-decyl-β-D-maltoside (n-decyl-β-D-maltopyranoside) is preferable.

The glycated protein cleavage method of the present invention is a method of cleaving a protein to obtain an amino acid or a peptide by a protease as described above, wherein the protein is subjected to protease treatment in the presence of the accelerating compound represented by the above Formula (I). As described above, by carrying out the protease treatment in the presence of the accelerating compound, the amino acid and the peptide can be obtained by the cleavage more efficiently than by carrying out the protease treatment in the absence of the accelerating compound. Thus, for example, an increase in an amount of the protease to be used for the treatment is not necessary. The mechanism that enables cleaving of the protein to obtain the amino acid or the peptide from the protein efficiently as described above is not known, but it can be assumed that the structure of the protein is changed into a structure that can be treated by the protease easily due to the coexistence of the accelerating compound. Incidentally, in the present invention, the subject to be cleaved is the "protein", but it includes a protein that is glycated partly, and the cleavage method of the present invention can be applied to the assay of a protein glycation degree as described below.

In the present invention, the protein to be cleaved is not limited particularly, but preferably is hemoglobin (Hb), for example. The amino acid or the peptide to be cleaved from the Hb by the protease is not limited particularly, and can be determined appropriately according to the protease to be used. In the case of presuming the below-described assay of the glycation degree, the amino acid generally is a β-chain N-terminal valine, a lysine or glycated products of them. An α-amino group of the glycated valine (fructosyl valine) at the β-chain N-terminal, and an ε-amino group of the glycated lysine are glycated. Moreover, the peptide generally is a peptide containing the β-chain N-terminal valine (hereinafter, also referred to as a "(β-chain N-terminal peptide"), or a peptide containing the lysine hereinafter, also referred to as a "lysine peptide"). The length of the peptide to be obtained by the cleavage is not limited particularly, and can be determined appropriately according to the kind of the protein and the protease to be used, but in the case of the Hb, a number of amino acid residues ranges, for example, 2 to 6, and more preferably ranges from 2 to 4, and it specifically is Fructosyl-Val-His, Fructosyl-Val-His-Leu, SEQ ID NO: 1 (Fructosyl-Val-His-Leu-Thr) or the like.

As described above, according to the present invention, a protein can be cleaved to obtain an amino acid or a peptide by the protease treatment in the presence of the accelerating compound efficiently, and the kind of the protease to be used is not limited particularly. That is, the kind of the protease can be determined appropriately according to the kind of the protein to be cleaved and the kind of the amino acid or the peptide to be obtained by the cleavage.

Examples of the protease include metalloprotease, serine protease, serine carboxypeptidase, proteinase K, bromelain, papain, trypsin derived from porcine pancreas, a protease derived from Bacillus subtilis, a protease derived from Aspergillus oryzae and the like, and endoprotease is preferably used. Commercially available products that can be used for the protease include, for example, metalloprotease (produced by Arkray, Inc.), protease A "Amano" G (produced by Amano Enzyme Inc.), protease M "Amano" G (produced by Amano Enzyme Inc.), protease S "Amano" G (produced by Amano Enzyme Inc.), peptidase R (produced by Amano Enzyme Inc.), papain M-40 (produced by Amano Enzyme Inc.), protease N (produced by Fluka Chemie AG), protease N "Amano" (produced by Amano Enzyme Inc.), metalloproteinase derived from the genus Bacillus (produced by Toyobo Co., Ltd., product name: Toyoteam), endoproteinase Glu-C (produced by Hoffmann-La Roche Inc.) and the like.

In particular, in the case where the protein is Hb and a β-chain N-terminal peptide is obtained by the cleavage, a protease that acts specifically on the β-chain N-terminal and catalyzes the cleavage of the N-terminal peptide (or example, JP 2000-300294 A and JP 2004-344052 A) is preferably used. By using this protease in the presence of the accelerating compound, even when the protein except for the β-chain N-terminal valine is glycated (for example, a lysine, an arginine or the like whose side chain group (ε-amino group) is glycated), the β-chain N-terminal peptide can be cleaved significantly swiftly and specifically. Moreover, examples of the protease that catalyzes the release by the cleavage of the β-chain N-terminal valine include proteases disclosed in WO 2000/50579 A1 (Japanese Patent No. 3668801), WO 2000/61732 A1, JP 2002-315600 A and the like.

In the case where the protein is Hb and a lysine or a peptide containing a lysine is released by the cleavage therefrom, for example, a protease disclosed in WO 2002/006519 A1 is preferably used. By using this protease in the presence of the accelerating compound, the lysine or the peptide containing the lysine can be released by the cleavage significantly swiftly and specifically.

Moreover, in the case where the protein is Hb and the protease releases by cleavage both of the β-chain N-terminal amino acid or peptide and the lysine or the lysine peptide, when carrying out the protease treatment in the presence of the accelerating compound, both of the cleavages are accelerated, and in particular, the cleavage acceleration of the β-chain N-terminal is more significant (several times to several tens times) than the cleavage acceleration of the lysine or the lysine peptide (for example, several times). Thereby, in particular, the cleavage product of the β-chain N-terminal can be obtained. Thus, even if using the protease that cleaves both of them similarly, the cleavage product of the β-chain N-terminal can be obtained more (for example, about ten times or more) than those of the lysine and the lysine peptide by the use of the accelerating compound in combination, so that the HbA1c corresponding to the glycation of the α-position amino group of the valine can be assayed while suppressing the influences of the lysine and the lysine peptide.

The protein cleavage method of the present invention can be carried out by adding the accelerating compound and the protease to a sample containing a protein, for example. Incidentally, the order of adding the accelerating compound and the protease is not limited at all, and they may be added at the same time or in any order.

The sample is not limited particularly, and may be a sample containing the target protein. In particular, when applying the sample to the assay of a Hb glycation degree as described below, for example, a whole blood sample, a blood cell sample, hemolyzed samples of them and the like may be used. A hemolysis method of the whole blood sample and the blood cell sample are not limited particularly, and may be, for example, a method utilizing an osmotic pressure difference, a method by ultrasonic waves and the like. In the case of utilizing the osmotic pressure difference, purified water of a volume of, for example, 2 to 100 times a volume of the whole blood (or the blood cell) may be added so as to cause the hemolysis. Alternatively, a surfactant may be added to the sample so as to cause the hemolysis.

An adding ratio of the accelerating compound in a reaction liquid of the protease treatment ranges, for example, from 0.01 mM to 200 mM, and preferably ranges from 0.4 mM to 100 mM. In the case where a protein concentration (for example, a Hb concentration) of the reaction liquid is 0.005 mM, the adding ratio of the accelerating compound ranges, for example, from 0.4 mM to 100 mM, and preferably ranges from 1 mM to 100 mM.

An adding ratio of the protease in the reaction liquid ranges, for example, 0.001 KU/L to 300,000 KU/L, preferably ranges from 0.01 KU/L to 30,000 KU/L, and particularly preferably ranges from 0.1 KU/L to 1,000 KU/L. In the case where the protein concentration (for example, a Hb concentration) of the reaction liquid is 0.005 mM, the adding ratio of the protease ranges, for example, from 0.01 KU/L to 300,000 KU/L, preferably ranges from 0.05 KU/L to 30,000 KU/L, and particularly preferably ranges from 0.1 KU/L to 10,000 KU/L.

Conditions for carrying out the protease treatment are not limited particularly, and for example, a treating temperature ranges, for example, from 10° C. to 40° C., and preferably ranges from 25° C. to 37° C. A treating time is not limited, in particular, an upper limit thereof is not limited, and for example, the protease treatment can be carried out in about 0.1 minutes to about 60 minutes. The treating time preferably ranges from 0.1 minutes to 45 minutes, more preferably ranges from 0.2 minutes to 20 minutes, and particularly preferably ranges from 0.2 minutes to 5 minutes. In the present invention, an amino acid and a peptide can be obtained by cleavage swiftly by carrying out the protease treatment in the presence of the accelerating compound represented by the above Formula (I) unlike in the conventional methods, so that the cleavage treatment can be achieved sufficiently even in the above-described treating time. From the fact that the conventional methods generally require, for example, 2 hours to 24 hours for the protease treatment so as to cleave a β-chain N-terminal of Hb, it can be seen that the cleavage can be achieved significantly swiftly.

The protease treatment preferably is carried out in, for example, a buffer solution, which may be a tris hydrochloric acid buffer solution, an EPPS buffer solution, a PIPES buffer solution, a phosphoric acid buffer solution, an ADA buffer solution, a citric acid buffer solution, an acetic acid buffer solution or the like. Moreover, the pH of the protease reaction liquid ranges, for example, 4 to 10, preferably ranges from 6 to 9, and for example, may be adjusted by the above-described buffer solutions.

Moreover, in the protein cleavage method of the present invention, the protease treatment may be carried out under the condition of further adding a nitro compound besides the accelerating compound. Examples of this nitro compound include nitrous acid and salts of the nitrous acid. The nitrous acid is not limited particularly, and may be, for example, potassium nitrite, amyl nitrite, butyl nitrite, nitroglycerin, sodium nitrite, paranitrochlorbenzene, trinitrotoluene, nitrobenzene and the like. An adding ratio of the nitro compound in the reaction liquid for the protease treatment is not limited particularly, and, for example, in the case where the protein concentration (for example, the Hb concentration) of the reaction liquid is 0.005 mM, the adding ratio of the nitro compound preferably is, for example, 0.005 mM or more, and more preferably ranges from 0.05 mM to 2 mM.

The protein cleavage method of the present invention enables cleaving of a protein to obtain an amino acid and a peptide efficiently as described above, and thus is applied usefully to the assay of the protein glycation degree by the above-described enzymatic method. Moreover, the protein cleavage method of the present invention is applied usefully not only to the enzymatic method, but also to, for example, an immunization method in which the cleaved glycated amino acid or the peptide obtained by the cleavage serves as an antigen, and further can improve the separation by the HPLC method and the electrophoresis. Thus, the protein cleavage method of the present invention is significantly useful as a treating process for a measurement sample in the various methods for assaying a protein glycation ratio. In addition, as described above, the HbA1c value of the Hb can be obtained from the glycation amount of the β-chain N-terminal valine, and a Lys glycation degree (GHbLys value) can be obtained from the glycation amount of the lysine. Thus, by cleaving a protein to obtain the β-chain N-terminal valine, the peptide containing the β-chain N-terminal valine, the lysine or the peptide containing the lysine from the Hb by the cleavage method of the present invention as described above, it is possible to assay the Hb glycation degree more accurately.

2. Method for Assaying Glycation Degree

As described above, the method for assaying the protein glycation degree of the present invention is a method for assaying a protein glycation degree including: a step of cleaving a protein with a protease; a step of allowing a FAOD to act on a glycated part of the obtained protein cleavage product; and a step of measuring a redox reaction between the glycated part and the FAOD so as to determine the protein glycation degree, wherein the protein is cleaved by the protein cleavage method of the present invention, and the FAOD is allowed to act on a glycated part of the amino acid or the peptide obtained.

(Method for Assaying HbA1c)

The method for assaying a protein glycation degree of the present invention will be explained by way of examples of assaying HbA1c of the glycated Hb.

In the case of assaying the HbA1c of the glycated Hb, a Hb cleavage product by a protease is a peptide containing a β-chain N-terminal glycated valine or a peptide containing the glycated valine, and a FAOD may be allowed to act on the glycated part of the β-chain N-terminal valine. Incidentally, as described above, the amino acid or the peptide to be obtained by cleavage can be determined according to the selection of a kind of the protease to be used.

The FAOD to be used in the method for assaying the HbA1c is not limited particularly, but preferably is an enzyme that catalyzes a reaction in which an α-amino group acts on the glycated amino acid or the glycated peptide so as to generate α-ketoaldehyde and hydrogen peroxide (hereinafter, referred to as a "FAOD-α". Such a catalytic reaction can be represented by a below Formula (1), for example.

$$R^1—CO—CH_2—NH—R^2+H_2O+O_2$$
$$\rightarrow R^1—CO—CHO+NH_2—R^2+H_2O_2 \quad (1)$$

In Formula (1) above, $R^1$ represents a hydroxyl group or a residue derived from a sugar before glycation reaction (i.e., sugar residue). The sugar residue ($R^1$) is an aldose residue when the sugar before the reaction is an aldose, and it is a ketose residue when the sugar before the reaction is ketose. For example, when the sugar before the reaction is a glucose, it takes a fructose structure after the reaction by an Amadori rearrangement. In this case, the sugar residue ($R^1$) becomes a glucose residue (aldose residue). This sugar residue ($R^1$) can be represented, for example, by $$—[CH(OH)]_n—CH_2OH$$

where n is an integer of 0 to 6.

In Formula (1), $R^2$ is not limited particularly, and may be an amino acid residue or a peptide residue represented by Formula (2) below, for example.

$$—CHR^3—CO—R^4 \quad (2)$$

In Formula (2), $R^3$ represents an amino acid side chain group, $R^4$ represents a hydroxyl group, an amino acid residue or a peptide residue, and can be represented, for example, by Formula (3) below. In Formula (3), n is an integer of 0 or more, $R^3$ represents an amino acid side chain group as in the above, and the amino acid side chain groups may be either the same or different.

$$—(NH—CHR^3—CO)_n—OH \quad (3)$$

Examples of the FAOD-A include product named FPOX-CE (produced by Kikkoman Corporation), product named FPOX-EE (produced by Kikkoman Corporation), a fructosyl amine oxidase described in WO 2004/029251 A1, fructosyl amine oxidases described in JP 2004-275013 A and JP 2004-275063 A, FAODs derived from the genus *Penicillium* (JP 8 (1996)-336386 A) and the like.

If using such a FAOD, for example, even when a part other than the β-chain N-terminal valine is glycated, the FAOD is not likely to act on the part other than the glycated part of the valine, so that the HbA1c can be assayed more accurately.

Incidentally, the FAOD further may have substrate specificity other than the above-described catalytic reaction (1). Such a FAOD may be, for example, a FAOD that acts both on the glycated α-amino group and the glycated amino acid side chain group (hereinafter, referred to as a "FAOD-aS"), and examples thereof include a commercially available product named FOD (produced by Asahi Chemical Industry Co., Ltd.), FAODs derived from the genus *Gibberella* (JP 8 (1996)-154672 A), FAODs derived from the genus *Fusarium* (JP 7 (1995)-289253 A), FAODs derived from the genus *Aspergillus* (WO 99/20039) and the like. In the case of such FAODs, for example, by selecting the kind of the protease appropriately and combining with the protease that specifically cleaves the protein to obtain the β-chain N-terminal amino acid and peptide, it is possible to suppress the action to other glycated part.

In the method for assaying the HbA1c, the measurement of a redox reaction between the glycated part and the FAOD may include, for example, measurement of an amount of hydrogen peroxide generated by the reaction and measurement of an amount of oxygen that is consumed by the reaction. The hydrogen peroxide amount can be measured by using, for example, a substrate that develops a color by oxidation with a peroxidase (POD), developing the color of the substrate by the reaction thereof with hydrogen peroxide, and measuring a level of this color.

The above-noted substrate that develops the color by oxidation (chromogenic substrate) is not particularly limited, and can be, for example, N,N,N',N',N'',N''-hexa(3-sulfopropyl)-4,4',4''-triaminotriphenylmethanehexasodium salt (for example, product named TPM-PS, manufactured by DOJINDO LABORATORIES), 10-(carboxymethylaminocarbonyl)-3,7-bis(dimethylamino)phenothiazine or its salt for example, product named DA-67, Wako Pure Chemical Industries, Ltd.), N-(carboxymethylaminocarbonyl)-4,4-bis (dimethylamino) diphenylamine sodium, orthophenylendiamin (OPD), a substrate of a combination of Trinder's reagent and 4-aminoantipyrine or the like. The Trinder's reagent can be, for example, phenols, phenol derivatives, aniline derivatives, naphthols, naphthol derivatives, naphthylamine, naphthylamine derivatives or the like. Other than the 4-aminoantipyrine noted above, it also is possible to use aminoantipyrine derivatives, vanillin diamine sulfonic acid, methylbenzothiazolinone hydrazone (MBTH), sulfonated methyl benzothiazolinone hydrazone (SMBTH) or the like.

Specific examples of the method for assaying the HbA1c will be shown below, but the present invention is not limited to these.

Firstly, similarly to the above, a Hb-containing sample is subjected to the protease treatment in the presence of the accelerating compound represented by the above Formula (I).

Then, β-chain N-terminal amino acid or a peptide fragment obtained by the protease treatment is treated by the FAOD. In the case where Fructosyl-Val-His is obtained from, for example, the Hb β-chain N-terminal by the protease treatment, a sugar that is bonded to an α-amino group of Val is isolated according to this FAOD treatment, thereby generating α-ketoaldehyde (sugar residue), Val-His and hydrogen peroxide.

The FAOD treatment preferably is carried out in a buffer solution similarly to the protease treatment described above. The buffer solution is not limited particularly, and buffer solutions similar to those for the above-described protease treatment can be used. Conditions for the FAOD treatment are not limited particularly, but a pH of a reaction liquid ranges, for example, from 6 to 9, and a treating temperature ranges, for example, from 10° C. to 38° C. and preferably ranges from 25° C. to 37° C. Also, a treating time is not limited particularly, and may range, for example, from 0.1 minutes to 60 minutes, and preferably ranges from 0.1 minutes to 5 minutes.

An adding ratio of the FAOD in the reaction liquid for the FAOD treatment ranges, for example, from 0.01 KU/L a to 50 KU/L, and preferably ranges from 0.5 KU/L to 10 KU/L.

Next, an amount of a hydrogen peroxide that is generated by the FAOD treatment is measured by using a POD and the chromogenic substrate. Incidentally, the hydrogen peroxide amount also can be measured not only by an enzymatic method using the POD or the like, but also by an electrical method.

The POD reaction preferably is effected in the buffer solution similarly to that in the protease treatment, and the above-described buffer solutions can be used. Conditions of the POD treatment are not limited particularly, and a pH of the reaction liquid ranges, for example, from 5 to 9, and a treating temperature ranges, for example, from 10° C. to 40° C., and preferably ranges from 25° C. to 37° C. Also, a treating time is not limited particularly, and ranges, for example, from 0.1 minutes to 5 minutes.

An adding ratio of the POD in the POD reaction liquid ranges, for example, from 0.01 KU/L to 300 KU/L, and preferably ranges from 0.5 KU/L to 40 KU/L. Moreover, an adding ratio of the chromogenic substrate in the reaction liquid ranges, for example, from 0.001 mM to 10 mM, and preferably ranges from 0.005 mM to 2 mM.

In the case of using the chromogenic substrate as described above, for example, the developed color (for example, an absorbance of the reaction liquid) may be measured by a spectrophotometer. Since the hydrogen peroxide amount corresponds to the glycation amount of the β-chain N-terminal valine of the Hb (glycation concentration: HbA1c concentration), the glycation amount of the valine can be calculated from the measured absorbance. Then, by calculating a ratio (%) between the glycation amount of the β-chain N-terminal valine of the Hb and a total Hb amount (Hb concentration) in the sample based on a below formula, the HbA1c (%) can be obtained. Incidentally, the Hb amount can be assayed by a conventionally known method by using a commercially available reagent kit.

HbA1c(%)=(glycation amount of β-chain N-terminal valine/Hb amount)×100

The Hb glycation amount can be calculated from the absorbance, by using a standard curve obtained by plotting a relationship between the known glycation amount of the β-chain N-terminal of the Hb and the absorbance. For example, an absorbance of a Hb reference solution whose β-chain N-terminal glycation amount is known is measured similarly to the above, and a standard curve showing a relationship between the measurement value of this reference solution and the known glycation amount is formed. Then, the absorbance measured as described above is substituted into this standard curve, thereby calculating the glycation amount of the β-chain N-terminal.

Moreover, according to the method described below, the Hb amount can be assayed more precisely by using a sample that is the same as the sample treated by the accelerating compound represented by the above Formula (I), and the HbA1c value can be obtained more precisely. That is, in the assay of the present invention, prior to the cleavage of the Hb by the protease, the accelerating compound represented by the above Formula (I) is added to the sample containing the Hb, an optical change amount of the sample to which the accelerating compound is added is measured, and the Hb amount in the sample is calculated from this optical change amount. Besides, after the Hb in the sample to which the compound is added is cleaved by the protease, the redox reaction between the glycated part and the FAOD is measured, thereby assaying the Hb glycation amount. And, it is preferable to obtain the HbA1c value (HbA1c value (%)) from the Hb amount and the glycation amount.

In this method, prior to the adding of the protease, the accelerating compound represented by the above Formula (I) is added to the sample containing the Hb is added, and for example, the absorbance of the sample is measured. And, the Hb amount may be obtained from the measured absorbance and the standard curve that is prepared in advance. As described above, by treating the Hb by the above-described compound, the Hb amount can be obtained easily and precisely. Although its mechanism is not known, it can be assumed that the structure of the hemoglobin is changed by the accelerating compound represented by the above Formula (I), whereby the unstable Hb is stabilized. For example, a plurality of the Hb containing samples with the known Hb amounts (Hb concentrations) are assayed by the above-described method, whereby the standard curve can be formed based on these measurement values and the known Hb amounts. Incidentally, the measurement wavelength of the absorbance is not limited particularly, and ranges, for example, from 400 nm to 660 nm, and a treating time of the sample by the compound ranges, for example, from 0.2 minutes to 30 minutes. In the case of assaying the Hb according to this method, the protease treatment and the like continuously are carried out similarly to the above, except for measuring the absorbance after adding the compound and before adding the protease, thereby obtaining the HbA1c concentration, so that the assay can be carried out more easily.

(Method for Assaying GHbLys)

Other than these, the method for assaying a glycation degree of the present invention may be, for example, an assay of GHbLys of the glycated Hb (Lys glycation degree). Since the above-described HbA1c responds to the change of a blood glucose level less sensitively, the HbA1c is not increased unless a high blood glucose level is maintained for several hours. On the other hand, the GHbLys reacts also to a high blood glucose state for several tens minutes sensitively. Thus, if assaying the GHbLys, for example, the high blood glucose can be detected, for example, after 1 hour to 2 hours from the meal, when the blood glucose level becomes high. Therefore, the GHLys is an indicator of the high blood glucose, and the assay thereof is significantly useful in the clinical field.

In the case of assaying the GHbLys of the glycated Hb, the Hb cleavage product obtained by the protease is a lysine whose ε-amino group is glycated or a glycated peptide containing the lysine, and the FAOD may be allowed to act on the glycated part of the lysine. Incidentally, as described above, the amino acid or the peptide to be cleaved can be determined by selecting the kind of the protease to be used.

The FAOD to be used for the method for assaying the GHbLys is not limited particularly, but preferably is at least an enzyme (FAOD-S) that acts on the amino acid or the peptide whose amino group (for example, an ε-amino group) of the amino acid side chain is glycated, and catalyzes a reaction represented by Formula (1') below.

The above Formula (1') is the same as the above Formula (1) except for the $R^2$. In the above Formula (1'), the $R^2$ can be shown by the below Formula (4'). In the below Formula (4'), "—$(CH_2)_4$—" represents a part of a side chain group of the lysine except for the glycated amino group.

Moreover, in the above Formula (4'), the $R^6$ is hydrogen, an amino acid residue or a peptide residue, and can be represented by below Formula (5'), for example. Incidentally, in the below Formula (5'), n is an integer of 0 or more, $R^3$ represents an amino acid side chain group similarly to the above, and all of the amino acid side chain groups may be the same or different.

Moreover, in the above Formula (4'), $R^7$ is a hydroxyl group, an amino acid residue or a peptide residue, and can be represented by below Formula (6'), for example. Incidentally, in the below Formula (6'), n is an integer of 0 or more, $R^3$ represents an amino acid side chain group similarly to the above, and all of the amino acid side chain groups may be the same or different.

(6')

Example of the FAOD-S that acts specifically on the above-described glycated amino acid side chain include FAODs derived from the genus *Fusarium* ("Conversion of Substrate Specificity of Amino Acid Oxidase Derived from *Fusarium oxysporum*" by Maki FUJIWARA et al., Annual Meeting 2000, The Society for Biotechnology, Japan) and the like.

Incidentally, the FAOD further may has substrate specificity other than the above (1'). Such a FAOD may be the FAOD-αS as described above. In the case of such a FAOD, it is possible to suppress the action on the other glycated part by selecting a protease that does not generate glycated amino acid whose α-position amino group at a N-terminal is glycated (for example, a protease that specifically cleaves a lysine and a peptide containing a lysine), such as the protease described in WO 2002/006519 A1, and combining the FAOD with the selected protease.

The GHbLys is assayed by treating the sample by the protease in the presence of the accelerating compound, cleaving to obtain the lysine or the peptide containing the lysine and treating it with the above-described FAOD. Then, the glycation amount of the lysine of the Hb is obtained by the method similar to the above, and a ratio (%) between the lysine glycation amount of this Hb and the total Hb amount in the sample are calculated based on the below formula, so that the GHbLys value (%) can be obtained.

GHbLys value(%)=(Lys glycation amount/Hb amount)×100

The Lys amount can be calculated from the absorbance, for example, by using a standard curve obtained by plotting a relationship between the known glycation amount of the lysine of the Hb and the absorbance. For example, a Hb reference solution whose Lys glycation amount is known is subjected to the absorbance measurement similarly to the above, and a standard curve showing a relationship between the measurement value of this reference solution and the known glycation amount is formed. Then, the absorbance that is measured as described above is substituted into this standard curve, thereby calculating the Lys glycation amount.

(Measurement of HbA1c and GhbLys)

The above-described two kinds of the glycation degrees of the Hb (HbA1c and GHbLys) also can be assayed continuously by using the same sample, by utilizing the substrate specificity of the FAOD. That is, the sample containing the Hb is subjected to the protease treatment in the presence of the accelerating compound so as to cleave the β-chain N-terminal valine or the β-chain N-terminal peptide, and the lysine or the peptide containing the lysine. Then, firstly, by treating by the FAOD-α that acts specifically on a glycated part of the α-amino group (for example, a glycated part of the valine) and is not likely to act on a glycated part of the amino acid side chain, the HbA1c is assayed. Thereafter, by further treating with the FAOD-S that acts specifically on the glycated part of the amino acid side chain (the glycated part of the lysine side chain) and is not likely to act on the glycated part of the α-amino group, the GHbLys may be assayed. Moreover, the order of the treatment by the FAODs is not limited to this, and for example, it is possible to assay the GHbLys by treating with the FAOD-S, and then assay the HbA1c by treating with the FAOD-A.

In the case of assaying the glycation degree of the protein in the blood cell such as the HbA1c and the GHbLys using a whole blood sample, a below-described effect further can be obtained by using the accelerating compound as described above. For the assay of the glycation degree of the protein in the blood cell, the whole blood sample is subjected to the hemolysis treatment so as to be used as a hemolyzed sample. At this time, the glycated protein (for example, a glycated albumin) in a serum coexists in the hemolyzed sample, but if the protease treatment is carried out in the presence of the accelerating compound, the above-described cleavage of the glycated Hb is accelerated, but the cleavage of the glycated albumin is suppressed, whose mechanism is not known though. Thus, for example, a problem that the glycated albumin and the like coexist and the FAOD acts also on the glycated part of the glycated albumin and the like can be avoided. Incidentally, such a problem occurs, for example, in the case where the protease acts on both of the Hb and the albumin, and the FAOD to be added later acts on both of the cleaved products of the proteins. Thus, this problem can be solved also by selecting the protease that selectively cleaves a target part (the glycated amino acid or the glycated peptide on which the FAOD acts) of the target protein as described above.

In the above-described assay of a glycation degree of the present invention, respective treating steps may be carried out separately as described above, and may be carried out at the same time, for example, in combinations described below. Also, the order of adding the protease, the FAOD, the POD and the chromogenic substrate are not limited particularly.

1: hemolysis treatment+protease treatment
2: protease treatment+FAOD treatment
3: FAOD treatment+POD treatment
4: protease treatment+FAOD treatment+POD treatment Next, the protein cleavage accelerating agent of the present invention is an accelerating agent for accelerating the cleavage of the amino acid or the peptide from the protein by the protease, as described above, and contains the accelerating compound represented by the above Formula (I).

The protein cleavage accelerating agent of the present invention is not limited as long as it contains the above-described compound, which may be the compound itself, and further may contain other material as long as the other material does not effect the cleavage of the β-chain N-terminal peptide and the like. Examples of the other material include nitro compounds such as nitrous acid. Incidentally, a concentration of the compound in the accelerating agent of the present invention is not limited particularly, and may be a concentration that becomes the above-described concentration after being added to the sample.

The present invention will be described more specifically below by way of examples and comparative examples, but the present invention is not limited to them.

EXAMPLE 1

Hb was cleaved in the presence of various compounds represented by the above Formula (I), and HbA1c was assayed by the enzymatic method. A sample and a reagent used in the assay and an assay method will be shown below. It should be noted that, as compounds of a below-described first reagent (R1-1), compounds of No. 1 to 9 described below were used, and No. 10 does not contain any compound (purified water).

TABLE 1

(First reagent: R1-1)

| Compound (No. 1 to 9) | 8.2 g/L |
|---|---|
| Tricine | 50 mmol/L (pH 8) |
| FAOD* | 2.5 KU/L |
| POD | 20 KU/L |

(Compound: No. 1 to 10)

| Compound | | Carbon number of R in the above Formula (I) |
|---|---|---|
| No. 1 | n-dodecyl-β-D-maltoside | 12 |
| No. 2 | sucrose monolaurate | 12 |
| No. 3 | n-decyl-β-D-maltoside | 10 |
| No. 4 | 6-cyclohexylhexyl-β-D-maltoside | 12 |
| No. 5 | n-nonyl-β-D-thiomaltoside | 9 |
| No. 6 | n-octyl-β-D-maltoside | 8 |
| No. 7 | n-heptyl-β-D-thioglucoside | 7 |
| No. 8 | cholic acid | |
| No. 9 | polyoxyethylenealkylether (product name: Brij 98) | |
| No. 10 | purified water (control) | |

(Second reagent: R2-1)

| Metalloprotease (produced by Arkray, Inc.) | 1300 KU/L |
|---|---|
| CaCl$_2$ | 5 mmol/L |
| MOPS | 150 mmol/L (pH 7.5) |
| Chromogenic reagent (Product name: TPM-PS, produced by Dojindo Laboratories, used also in the following examples) | 0.25 mmol/L |

FAOD*: product name: FPOX-CE (produced by Kikkoman Corporation)

(Sample)

(1) HbA0 Sample

Hb of a normal subject was processed by a strong cation exchange column (product name: POROS-HS50, produced by Applied Biosystems), and a fraction of HbA0 was purified and collected by a typical method. A HbA1c value (%) of this sample was 0%, and a hemoglobin concentration thereof was 2 g/L.

(2) Low HbA1c Sample

To blood of a diabetic patient, purified water in an amount equivalent to an amount of the blood was added so as to hemolyze blood cells, and blood cell membranes were removed by centrifugation, thereby preparing a sample. A HbA1c value (%) of this sample was 12%, and a hemoglobin concentration thereof was 2 g/L.

(3) High HbA1c Sample

The Hb of a normal subject was processed by a strong cation exchange column (product name: POROS-HS50, produced by Applied Biosystems), and a fraction of the HbA1c was purified and collected by a typical method. A HbA1c value (%) of this sample was 30%, and a hemoglobin concentration thereof was 2 g/L.

Incidentally, the HbA1c values (%) of the respective samples were assayed by using an assay apparatus (product name: HA-8160, produced by Arkray, Inc.), and the hemoglobin concentrations thereof were assayed by a typical method of an alkali hematin assay.

(Method)

15 μm of the respective samples and 76 μm of the respective first reagents (R1-1) were mixed and were incubated at 37° C. for 5 minutes, and thereafter, 26 μm of the second reagent (R2-1) was added thereto, which further were subjected to the protease treatment at 37° C. and effected chromogenic reactions. Then, absorbance ($A_0$) at a wavelength of 571 nm in reaction liquids immediately before adding the second reagent and absorbance ($A_{1.5}$) at a wavelength of 571 nm in the reaction liquids after 1.5 minutes from the adding of the second reagent were measured with a biochemical automatic analyzer (product name: JCA-BM8, produced by JEOL Ltd., used also in the following examples), and a difference thereof ($A_{1.5}-A_0$) was obtained. Results of them will be shown in Table 2 below.

TABLE 2

| | Absorbance(Abs.) | | |
|---|---|---|---|
| Compound No. | HbA0 HbA1c value (%) = 0% | Low HbA1c HbA1c value (%) = 12% | High HbA1c HbA1c value (%) = 40% |
| 1 | 0.010 | 0.016 | 0.027 |
| 2 | 0.010 | 0.020 | 0.028 |
| 3 | 0.011 | 0.020 | 0.022 |
| 4 | 0.008 | 0.016 | 0.022 |
| 5 | 0.011 | 0.018 | 0.020 |
| 6 | 0.001 | 0.002 | 0.002 |
| 7 | 0.003 | 0.004 | 0.003 |
| 8 | 0.003 | 0.002 | 0.004 |
| 9 | 0.004 | 0.006 | 0.005 |
| 10 | 0.001 | 0.001 | 0.002 |

As shown in Table 2 above, by using the compounds (No. 1 to 5) represented by the above Formula (I), the absorbance was increased according to the increase of the HbA1c values (%) in the respective samples. This means that a β-chain N-terminal peptide as a feature of the HbA1c was obtained by cleavage in a short period of time (5 minutes), and the FAOD acted thereon. On the other hand, in the case of using the compound whose carbon number of R (straight-chain alkyl) in the above Formula (I) was less than 9 (No. 6 and 7), cholic acid (No. 8) and a general surfactant having no sugar residue (No. 9), and in the absence of the compound represented by the above Formula (I) (No. 10), the increase of the absorbance according to the increases of the HbA1c values (%) in the respective samples was not found. That is, the N-terminal peptide could not be obtained by cleavage efficiently in a short period of time.

EXAMPLE 2

First reagents (R1-2) were prepared by adding NaNO$_2$ further to the first reagents (R1-1) in Example 1, and absorbance thereof was measured similarly to Example 1. Results will be shown in Table 4 below. Incidentally, the results of Example 1 using the first reagents (R1-1) also will be shown in Table 4 below.

TABLE 3

(First reagent: R1-1 to R1-2)

| | | R1-1 | R1-2 |
|---|---|---|---|
| Compound (No. 1 to 8) | 8.2 g/L | + | + |
| Tricine | 50 mmol/L (pH 8) | + | + |
| NaNO$_2$ | 14 mmol/L | − | + |
| FAOD* | 2.5 KU/L | + | + |
| POD | 20 KU/L | + | + |

FAOD*: product name: FPOX-CE (produced by Kikkoman Corporation)

TABLE 4

| | R1-1<br>(no NaNO$_2$ added)<br>Absorbance (Abs.) | | R1-2<br>(NaNO$_2$ added)<br>Absorbance (Abs.) | |
|---|---|---|---|---|
| No. | HbA0<br>HbA1c<br>value<br>(%) = 0% | High HbA1c<br>HbA1c value<br>(%) = 40% | HbA0<br>HbA1c<br>value<br>(%) = 0% | High HbA1c<br>HbA1c value<br>(%) = 40% |
| 1 | 0.010 | 0.027 | 0.002 | 0.080 |
| 2 | 0.010 | 0.028 | 0.003 | 0.081 |
| 3 | 0.011 | 0.022 | 0.003 | 0.050 |
| 4 | 0.008 | 0.022 | 0.003 | 0.056 |
| 5 | 0.011 | 0.020 | 0.003 | 0.044 |
| 6 | 0.001 | 0.002 | 0.002 | 0.006 |
| 7 | 0.003 | 0.003 | 0.004 | 0.004 |
| 8 | 0.003 | 0.004 | 0.002 | 0.003 |
| 9 | 0.004 | 0.005 | 0.004 | 0.012 |
| 10 | 0.001 | 0.002 | 0.002 | 0.003 |

As shown in Table 4 above, a further increase of the absorbance was found by further adding nitrous acid. From this result, it can be seen that the β-chain N-terminal peptide obtaining can be accelerated, by the coexistence of the nitrous acid with the compound represented by the above Formula (I).

EXAMPLE 3

The accuracy of the method for assaying HbA1c was checked by using a reference material of the HbA1c.

(Sample)

As the reference material, a real sample reference material for assaying the HbA1c (JDS HbA1c Lot2, produced by Health Care Technology Foundation), a certified HbA1c calibrator (HbA1c standardized IFCC, produced by Working Group) and a certified HbA1c control (HbA1c standardized IFCC, produced by Working Group) were used, and a reference sample was obtained by diluting them 25-fold with the purified water.

(Method)

13 µL of the respective reference samples and 78 µL of first reagents (R1-3) were mixed and were incubated at 37° C. for 5 minutes, and further, 26 µL of the second reagent (R2-1) that was used also in Example 1 was added thereto, which were subjected to the protease treatment at 37° C. and effected chromogenic reactions. Then, absorbance ($A_0$) at a wavelength of 571 nm in reaction liquids immediately before adding the second reagent and absorbance ($A_{1.5}$) at a wavelength of 571 nm in the reaction liquids after 1.5 minutes from the adding of the second reagent were measured by using the biochemical automatic analyzer, and differences thereof ($A1.5-A_0$) were obtained. Then, HbA1c values (%) were calculated from these absorbance differences as described below, and a correlation between these calculation results and the indicated HbA1c values (%) of the reference samples was checked. Results of the HbA1c values (%) obtained from the absorbance differences and the indicated values will be shown in Table 6 below and the graph of FIG. 1.

(HbA1c Value (%) Calculation Method)

By multiplying the indicated values of the Hb concentrations of the reference samples and the indicated values of the HbA1c values (%), the HbA1c concentrations were calculated. These values were indicated values of the HbA1c concentrations. From the indicated HbA1c concentration values of these reference samples and the absorbance differences of the reference samples, a linear correlation function was obtained, which was used as a standard curve. Then, HbA1c concentrations were calculated from the absorbance differences ($A_{1.5-A0}$) by using this standard curve, and these calculated HbA1c concentration values were divided by the Hb concentrations and were multiplied by 100, thereby obtaining the HbA1c values (%). Incidentally, the Hb concentration was calculated as follows. Firstly, a linear correlation function between the Hb concentration and the indicated value was obtained by using the absorbance ($A_0$) at the wavelength of 571 nm in the reaction liquid immediately before adding the second reagent, so that the standard curve was formed. Then, by using this standard curve, the Hb concentration was calculated from the $A_0$.

TABLE 5

(First reagent: R1-3)

| | |
|---|---|
| n-dodecyl-β-D-maltoside | 10 g/L |
| MOPS | 50 mmol/L (pH 7.5) |
| NaNO$_2$ | 14 mmol/L |
| FAOD* | 2.5 KU/L |
| POD | 10 KU/L |

FAOD*: product name: FPOX-CE (produced by Kikkoman Corporation)

TABLE 6

| Reference sample | Indicated value of reference sample HbA1c value (%) | Calculation value from absorbance HbA1c value (%) |
|---|---|---|
| JDS Lot2 Level 1 | 2.57 | 2.43 |
| JDS Lot2 Level 2 | 4.01 | 3.94 |
| JDS Lot2 Level 3 | 6.08 | 6.18 |
| JDS Lot2 Level 4 | 8.81 | 8.33 |
| JDS Lot2 Level 5 | 11.75 | 12.20 |
| IFCC calibrator Level 1 | 3.16 | 3.03 |
| IFCC calibrator Level 2 | 4.13 | 3.91 |
| IFCC calibrator Level 3 | 5.08 | 5.11 |
| IFCC calibrator Level 4 | 6.34 | 6.52 |
| IFCC calibrator Level 5 | 7.52 | 7.53 |
| IFCC calibrator Level 6 | 8.74 | 9.07 |
| IFCC calibrator Level 7 | 9.89 | 9.79 |
| IFCC calibrator Level 8 | 12.03 | 11.42 |
| IFCC control Low | 3.10 | 3.33 |
| IFCC control Middle | 5.10 | 5.41 |
| IFCC control High | 7.50 | 7.63 |

Figure 1:
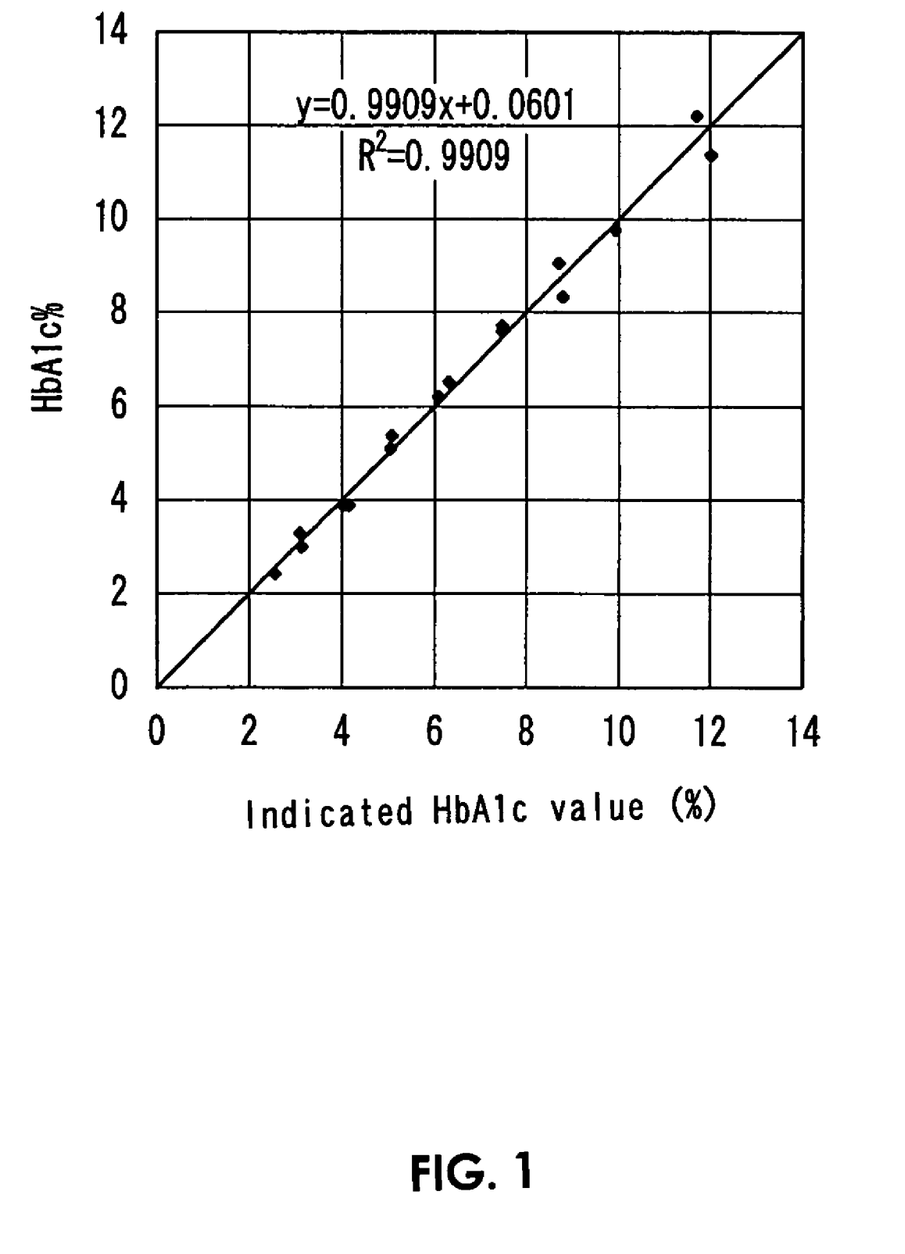
FIG. 1 is a graph showing a correlation between an assayed HbA1c value (%) and an indicated HbA1c value of a reference sample in an example of the present invention.

As shown in the figure, a correlation coefficient between the calculation values from the absorbance and the indicated values of the reference samples was as high as 0.995, and the significantly high correlation was exhibited. From this result, it can be confirmed that the HbA1 value (%) can be assayed precisely according to the assay method of the present invention.

EXAMPLE 4

Hb was subjected to the protease treatment in the presence of n-dodecyl-β-D-maltoside so as to check whether an N-terminal dipeptide (Fructosyl-Val-His) was obtained by cleavage or not.

TABLE 7

(First reagent: R1-4)

| | |
|---|---|
| n-dodecyl-β-D-maltoside | 10 g/L |
| MOPS | 50 mmol/L (pH 7.5) |

TABLE 7-continued

| | |
|---|---|
| NaNO$_2$ | 14 mmol/L |
| (Second reagent: R2-4) | |
| Metalloprotease (produced by Arkray, Inc.) | 1300 KU/L |
| CaCl$_2$ | 5 mmol/L |
| MOPS | 150 mmol/L (pH 7.5) |

(Sample)

Product named Hemoglobin A1c P186-4 (HbA1c value (%)=44%, produced by Scipac Ltd.) and product named Hemoglobin (Essentially HbA1c Free) P2111-3 (HbA1c value (%)=0%, produced by Scipac Ltd.) were used.

(HPLC)

As a HPLC column, product named YMC PACK ODS-AM 250×6.0 (produced by YMC Co., Ltd.) was used, and a liquid A (volume ratio of KH$_2$PO$_4$:methanol=100:2) and a liquid B (volume ratio of KH$_2$PO$_4$:methanol=100:100) were used as an eluant. A sample amount was 100 μL, a detection wavelength was 215 nm, a flow velocity of the eluant was 1 mL/min, the liquid A (100%) was used from starting of the elution to 2 minutes, thereafter, the volume ratio of the liquid B was increased to 100% in 10 minutes, and the liquid B (100%) was used further for 15 minutes. As the reference sample of the HPLC, Val-His (produced by BACHEM AG) and Fructosyl-Val-His that is prepared from the Val-His and the glucose by a typical method were used. It should be noted that a retention time of the Val-His was about 6.4 minutes, and a retention time of the Fructosyl-Val-His was about 10.3 minutes.

Figure 2:
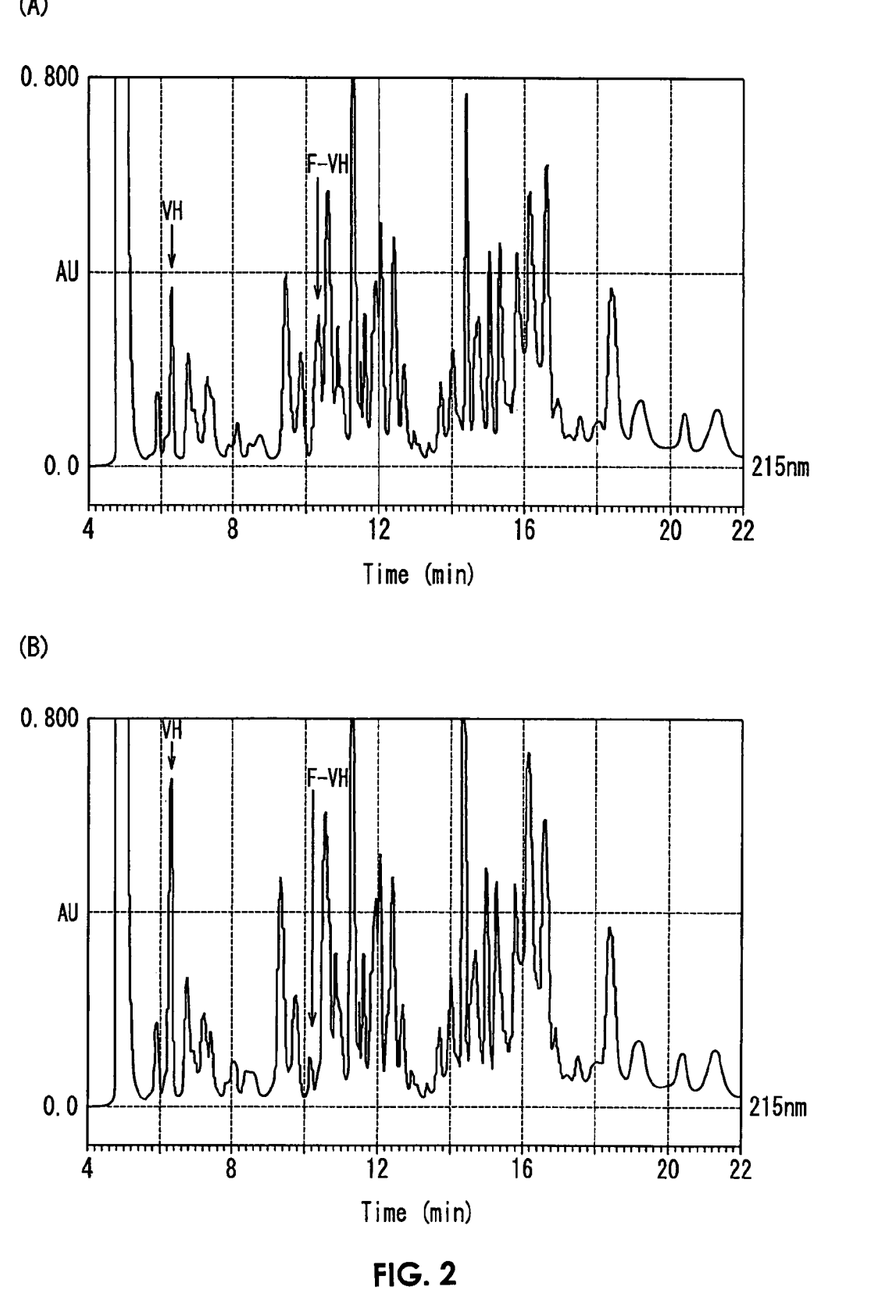
FIG. 2 is a chromatogram of HPLC in another example of the present invention, more specifically.

520 μL of the respective samples and 1560 μL of the first reagent (R1-4) were mixed and were incubated at 37° C. for 5 minutes, and thereafter, 520 μL of the second reagent (R2-4) further was added thereto, which was subjected to the protease treatment at 37° C. for 1 minute. This reaction liquid was transferred to an ultrafree 4 filter unit (molecular weight: 5000, produced by Millipore Corporation) and was processed by centrifugal filtration (4° C., 3000 rpm, 20 minutes), and the thus obtained filtrate as a sample was subjected to the HPLC. Results thereof will be shown in FIG. 2. The figure shows chromatograms of the samples, FIG. 2A shows a result obtained by using the sample with the HbA1c value (%) of 44%, and FIG. 2B shows a result obtained by using the sample with the HbA1c value (%) of 0%.

Comparing FIG. 2A showing the result of the sample with the HbA1c value (%) of 44% with FIG. 2B showing the result of the sample with the HbA1c value (%) of 0%, a peak of the Fructosyl-Val-His (F-VH) higher than a peak of the Val-His (VH) was detected. From this fact, it can be realized that the glycated Val-His (Fructosyl-Val-His) was obtained by the cleavage efficiently in a significantly short period of time (1 minute) from the N-terminal of the HbA1c.

EXAMPLE 5

As the compound, dodecylmaltosides were examined. Incidentally, as the compounds for a below-described first reagent (R1-5), compounds (No. 1 to 6) shown in the below table were used.

TABLE 8

(First reagent: R1-5)

| | |
|---|---|
| Compound (No. 1 to 6) | 5.2 g/L |
| Tricine | 50 mmol/L (pH 8) |

TABLE 8-continued

| | |
|---|---|
| NaNO$_2$ | 3 mmol/L |
| DTPA | 0.2 g/L |
| POD | 20 KU/L) |

(Compound: No. 1 to 6)

| Compound | | Carbon number of R in the above Formula (I) |
|---|---|---|
| No. 1 | octyl-β-D-maltoside | 8 |
| No. 2 | 5-cyclohexylpentyl-β-D-maltoside | 11 |
| No. 3 | undecyl-β-D-maltoside | 11 |
| No. 4 | dodecyl-αβ-D-maltoside | 12 |
| No. 5 | hexadecyl-β-D-maltoside | 16 |
| No. 6 | 3-oxatridecyl-α-D-mannoside | 10 |

(Second reagent: R2-5)

| | |
|---|---|
| Metalloprotease (produced by Arkray, Inc.) | 1300 KU/L |
| CaCl$_2$ | 5 mmol/L |
| MOPS | 150 mmol/L |
| TPM-PS | 0.25 mmol/L |

(Third reagent: R3-5)

| | |
|---|---|
| FAOD** | 52 KU/L |
| FAOD* | 13 KU/L |
| MOPS | 20 mmol/L |

FAOD**: product name: FAOD3 (produced by Arkray, Inc., used also in the following examples)
FAOD*: product name: FPOX-CE (produced by Kikkoman Corporation)

(Sample)

From whole blood collected from a normal subject and whole blood collected from a diabetic patient, blood cells were collected respectively. Then, an equivalent amount of purified water was added to the blood cells so as to hemolyze the blood cells, and blood cell membranes were removed by centrifugation, thereby obtaining respective samples. A HbA1c value (%) of the sample derived from the normal subject was 3.5%, and a HbA1c value (%) of the sample derived from the diabetic patient was 8.5%.

(Method)

13 μL of the respective samples and 78 μL of the respective first reagents (R1-5) were mixed and were incubated at 37° C. for 5 minutes, and thereafter, 26 μL of the second reagent (R2-5) further was added thereto, which were subjected to the protease treatment at 37° C. for 4 minutes. Further, 15 μL of the third reagent (R3-5) were added thereto so as to effect chromogenic reactions. Then, absorbance ($A_0$) at a wavelength of 571 nm in reaction liquids immediately before adding the third reagent and absorbance ($A_{1.5}$) at a wavelength of 571 nm in the reaction liquids after 1.5 minutes from the adding of the third reagent were measured with the biochemical automatic analyzer, and differences therebetween ($A1.5-A_0$) were obtained. Results will be shown in Table 9 below.

TABLE 9

| | | Absorbance (Abs.) | |
|---|---|---|---|
| Compound No. | | Normal subject | Diabetic patient |
| 1 | C8 | 0.013 | 0.015 |
| 2 | C11 | 0.031 | 0.040 |
| 3 | C11 | 0.034 | 0.047 |
| 4 | C12 | 0.033 | 0.045 |
| 5 | C16 | 0.021 | 0.031 |
| 6 | C10 | 0.020 | 0.030 |

As shown in the above Table 9, in the case of using the compound (No. 1) whose carbon number of straight-chain alkyl was less than 9, although the HbA1c values of the samples from the normal subject and the diabetic patient were different, only the similar levels of absorbance were obtained. This shows that the β-chain N-terminal peptide could not be released by the cleavage efficiently. On the other hand, in the case of using the compounds represented by the above Formula (I) (No. 2 to 6), a difference in absorbance was found between both of the samples, which shows that the β-chain N-terminal could be released by the cleavage efficiently.

EXAMPLE 6

Kinds of the proteases to be combined with n-dodecyl-β-D-maltoside were examined.

TABLE 10

| (First reagent: R1-6) | |
|---|---|
| n-dodecyl-β-D-maltoside | 4.8 g/L |
| Tricine | 50 mmol/L (pH 8) |
| NaNO$_2$ | 14 mmol/L |
| FAOD* | 10 KU/L |
| POD | 20 KU/L |

| (Second reagent: R2-6) | |
|---|---|
| Protease | predetermined amount |
| CaCl$_2$ | 5 mmol/L |
| MOPS | 150 mmol/L |
| TPM-PS | 0.25 mmol/L |

FAOD*: product name: FPOX-CE (produced by Kikkoman Corporation)

For the above-described second reagent (R2-6), below-described proteases (No. 1 to 6) were used.

| No. 1 | metalloprotease (produced by Arkray, Inc.) | 1300 KU/L |
|---|---|---|
| No. 2 | Protease A "Amano" G (produced by Amano Enzyme Inc.) | 0.1 g/L |
| No. 3 | Protease M "Amano" G (produced by Amano Enzyme Inc.) | 0.1 g/L |
| No. 4 | Protease S "Amano" G (produced by Amano Enzyme Inc.) | 0.1 g/L |
| No. 5 | Peptidase R (produced by Amano Enzyme Inc.) | 0.1 g/L |
| No. 6 | Papain M-40 (produced by Amano Enzyme Inc.) | 0.1 g/L |

(Sample)

(1) HbA0 Sample

Product named Hemoglobin (Essentially HbA1c Free) P2111-3 (HbA1c value (%)=0%, produced by Scipac Ltd) was diluted 25-fold (volume) with purified water, thereby preparing a sample. The HbA1c value (%) of this sample was 0%.

(2) Low HbA1c Sample

To blood cells of a diabetic patient, purified water with a volume of 25 times that of the blood cells was added so as to hemolyze them, thereby preparing a sample. The HbA1c value (%) of this sample was 8.5%.

(3) High HbA1c Sample

Product named Hemoglobin A1c P186-4 (HbA1c value (%)=44%, produced by Scipac Ltd) was diluted 25-fold (volume) with purified water, thereby preparing a sample. The HbA1c value (%) of this sample was 44%.

(Method)

13 μL of the respective samples and 78 μL of the first reagent (R1-6) were mixed and were incubated at 37° C. for 5 minutes, and thereafter, 26 μL of the second reagent (R2-6) further was added thereto, which were subjected to the protease treatment at 37° C. and effected the chromogenic reactions. Then, absorbance ($A_0$) at a wavelength of 571 nm in reaction liquids immediately before adding the second reagent and absorbance ($A_{10}$) at a wavelength of 571 nm in the reaction liquids after 10 minutes from the adding of the second reagent were measured with the biochemical automatic analyzer, and differences therebetween ($A_{10}–A_0$) were obtained. Results will be shown in Table 11 below.

TABLE 11

| | Absorbance (Abs.) | | |
|---|---|---|---|
| Protease No. | HbA0 HbA1c value (%) = 0% | Low HbA1c HbA1c value (%) = 8.5% | High HbA1c HbA1c value (%) = 44% |
| 1 | 0.020 | 0.030 | 0.034 |
| 2 | 0.015 | 0.016 | 0.025 |
| 3 | 0.026 | 0.017 | 0.038 |
| 4 | 0.013 | 0.015 | 0.026 |
| 5 | 0.013 | 0.011 | 0.025 |
| 6 | 0.014 | 0.016 | 0.026 |

As shown in the above Table 11, it was realized that the respective kinds of proteases can be used, from the result that the absorbance was increased according to the increases of the HbA1c values (%) of the respective samples.

EXAMPLE 7

The Hb was subjected to the protease treatment in the presence of dodecyl-β-D-maltoside, and the obtained fragment was used for assaying the HbA1c with the immunization method.

TABLE 12

| (Protease reagent) | | | |
|---|---|---|---|
| | | Reagent | |
| | | A | B |
| Dodecyl-β-D-maltoside | 5 g/L | – | + |
| Tris-HCl | 20 mmol/L (pH 7) | + | + |
| Protease* | 0.2 mg/L | + | + |

Protease*: product named endoprotease Glu-C (produced by Hoffmann-La Roche Inc.)
Latex reagent: product named COBAS reagent HbA1c, R2 (produced by Hoffmann-La Roche Inc.)
Hemagglutination reagent: product named COBAS reagent HbA1c, R3 (produced by Hoffmann-La Roche Inc.)
Hemolysis reagent: product named HbA1c hemolysis reagent "ROCHE" (produced by Hoffmann-La Roche Inc.)

(Reference Sample, Blood Cell Sample)

A reference material was obtained by glycating an α-amino group of a Val in a peptide sequence of the β-chain N-terminal of the Hb (six residues: Val-His-Leu-Thr-Pro-Glu) by a typical method, which was dissolved in the hemolysis reagent so as to have a concentration of 6 μmol/L, thereby preparing a reference sample. Moreover, as a blood cell sample, blood cells of a diabetic patient (HbA1c value (%)=11.6%, HbA1c concentration=5.10 μmol/L, Hb concentration=2.2 mmol/L) were used.

10 μl of the samples (the reference sample, the blood cell sample) and 500 μL of protease reagents (reagent A (–), reagent B (+)) were mixed so as to prepare a hemolyzed sample, which were treated at 37° C. for a predetermined period of time (10 minutes, 150 minutes, 270 minutes). 120 μL of purified water was added to 30 μL of the treated hemolyzed samples so as to prepare diluted solutions, 80 μL of the latex reagent was added to 2 μm of the diluted solutions, which were treated at 37° C. for 5 minutes, and further, 16 μL of the hemagglutination reagent was added thereto. Then, absorbance changes (at an wavelength of 545 nm) of the reaction liquids were measured after 30 seconds to 60 seconds from the adding of the hemagglutination reagent. Subsequently, according to an instruction manual of a reagent kit (COBAS reagent HbA1c), a HbA1c concentration was calculated from the absorbance. Moreover, absorbance measurement was carried out similarly, using purified water as a control instead of the sample. Results will be shown in Table 13 below. In the below table, (+) represents addition of dodecyl-β-D-maltoside, and (−) represents no addition of dodecyl-β-D-maltoside.

diabetic patient. From this result, it can be concluded that the Hb cleavage method of the present invention can cleave the protein to obtain the β-chain N-terminal efficiently, and is effective for the HbA1c assay by the immunization method.

EXAMPLE 8

Effects of the HbA1c assay by the method of the present invention using the accelerating compound was compared with those by a method of accelerating the cleavage by the protease by using a tetrazolium compound, which has been filed separately by the applicant of the present invention (WO

TABLE 13

(A) Reference sample

| | Protease treating time 10 minutes | |
|---|---|---|
| | Reagent A (−) | Reagent B (+) |
| Purified water (Abs.) | 0.594 | 0.596 |
| Reference sample (Abs.) | 0.475 | 0.482 |
| Difference from purified water (Abs.) | 0.119 | 0.116 |

(B) Blood cell sample

| | Protease treating time | | | | | |
|---|---|---|---|---|---|---|
| | After 10 minutes | | After 150 minutes | | After 270 minutes | |
| | Reagent A (−) | Reagent B (+) | Reagent A (−) | Reagent B (+) | Reagent A (−) | Reagent B (+) |
| Purified water (Abs.) | 0.594 | 0.596 | 0.594 | 0.596 | 0.594 | 0.596 |
| Blood cell sample (Abs.) | 0.586 | 0.564 | 0.580 | 0.517 | 0.575 | 0.497 |
| Difference from purified water (Abs.) | 0.008 | 0.032 | 0.014 | 0.078 | 0.019 | 0.099 |
| Concentration conversion value (μmol/L) | 0.40 | 1.66 | 0.70 | 4.03 | 0.96 | 5.07 |

As shown in the above Table 13(B), in the case of using the reagent B (+) to which dodecyl-β-D-maltoside was added, a difference in absorbance between the blood cell sample and the purified water was increased according to the increase of the protease treating time. Moreover, the HbA1c concentration that was converted from the absorbance difference in the case of treating for 270 minutes by using the results (absorbance differences) of the reference samples shown in the above Table 13(A) was 5.07 μmol/L, which substantially coincides with the preobtained HbA1c concentration (5.1 μmol/L) of the sample from the diabetic patient, so that it is found that the β-chain N-terminal peptide could be obtained by cleavage completely by the treatment for 270 minutes. On the other hand, in the case of using the reagent A (−) to which no dodecyl-β-D-maltoside was added, the gentle increase of the absorbance according to the increase of the protease treating time was found, but a HbA1c concentration conversion value in the case of carrying out the protease treatment for 270 minutes was 0.96 μmol/L, which was as small as about ⅕ of the preobtained HbA1c concentration of the sample from the 02/27012). As the tetrazolium compound, 2-(4-iodophenyl)-3-(2,4-dinitrophenyl)-5-(2,4-disulphophenyl)-2H-tetrazolium monosodium salt (product name: WSP-3, produced by Dojindo Laboratories) was used.

As the compound for a first reagent (R1-8) described below, n-dodecyl-β-D-maltoside (Compound No. 1) was used as a working example, and WSP-3 (Compound No. 2) was used as a reference example. Moreover, as a comparative example, purified water (No. 3) to which the compound was not added was used.

TABLE 14

(First reagent: R1-8)

| Compound (No. 1 and 2) | Predetermined amount |
|---|---|
| PIPES | 30 mmol/L (pH 7) |
| FAOD* | 1.5 KU/L |
| POD | 10 KU/L |

TABLE 14-continued (Compound: No. 1 to 3)

| Compound | | |
|---|---|---|
| No. 1 | n-dodecyl-β-D-maltoside | 2.5 g/L |
| No. 2 | WST-3 | 2 mmol/L |
| No. 3 | Not added (purified water) | |

| (Second reagent: R2-8) | |
|---|---|
| Metalloprotease (produced by Arkray, Inc.) | 4000 KU/L |
| CaCl$_2$ | 5 mmol/L |
| Tris | 200 mmol/L |
| MES | 30 mmol/L (pH 5.5) |
| Chromogenic reagent | 0.25 mmol/L |
| (Product name: DA-67, produced by Wako Pure Chemical Industries, Ltd., used also in the following examples) | |

FAOD*: product name: FPOX-CE (produced by Kikkoman Corporation)

(Sample)

Whole blood of a normal subject was diluted 31-fold with purified water and products listed below were diluted 31-fold with purified water, thereby preparing samples. As a control for the samples, purified water was used.

IFCC control Barcelona, Low HbA1c, Normal Hemoglobin (HbA1c value (%)=3.2%)

IFCC control Barcelona, Medium HbA1c, Medium Hemoglobin (HbA1c value (%)=5.1%)

IFCC control Barcelona, High HbA1c, Normal Hemoglobin (HbA1c value (%)=7.5%)

(Method)

6.5 μL of the respective samples and 6.5 μL of the purified water were mixed, and 78 μL of the respective first reagents (R1-8) further were mixed therein. After incubating these mixture solutions at 37° C. for 5 minutes, 19.5 μL of the second reagent (R2-8) was added thereto, which were subjected to the protease treatment at 37° C. and effected chromogenic reactions. Then, absorbance ($A_0$) at a wavelength of 658 nm in a reaction liquid immediately before adding the second reagent and absorbance ($A_5$) at a wavelength of 658 nm in the reaction liquid after 5 minutes from the adding of the second reagent were measured by using a biochemical automatic analyzer (product name: JCA-BM8, produced by JEOL Ltd.), and differences thereof ($A_5$–$A_0$) were obtained. Results of them will be shown in Table 15 below. In the below Table 15, numerals in brackets represent differences from the result obtained by using the sample control (purified water).

TABLE 15

| | | Absorbance (Abs.) | | | |
|---|---|---|---|---|---|
| Compound No. | Purified water | Whole of normal subject | IFCC Low 3.2% | IFCC Medium 5.1% | IFCC High 7.5% |
| 1 n-dodecyl-β-D-maltoside | 0.011 | 0.029 (0.018) | 0.025 (0.014) | 0.037 (0.026) | 0.050 (0.039) |
| 2 WST-3 | 0.029 | 0.026 (−0.003) | 0.025 (−0.004) | 0.026 (−0.003) | 0.026 (−0.003) |
| 3 Not added | 0.014 | 0.015 (0.001) | 0.014 (0.000) | 0.015 (0.001) | 0.015 (0.001) |

As shown in the above Table 15, the absorbance was not increased in the comparative example (No. 3) in which the accelerating compound was not added. On the other hand, the absorbance was increased according to the increase of the HbA1c values (%) of the respective samples in the working example (No. 1) in which n-dodecyl-β-D-maltoside was used. This means that the β-chain N-terminal peptide that is the feature of the HbA1c was obtained by cleavage in a short period of time (5 minutes), and the FAOD acted thereon. Further, in the reference example (No. 2) in which WST-3 was added, the increase of the absorbance according to the increases of the HbA1c values (%) was not found in the treatment for such a significantly short period of time of 5 minutes. From the results described above, with the n-dodecyl-β-D-maltoside, the time required for the cleavage can be reduced significantly compared with that in the conventional technique.

EXAMPLE 9

The Hb was cleaved in the presence of n-dodecyl-β-D-maltoside, and the HbA1c and GHbLys were assayed by the enzymatic method continuously. Incidentally, as the FAOD, FPOX-CE (product name, produced by Kikkoman Corporation) that acts specifically on a peptide whose α-position is glycated (β-chain N-terminal peptide) and FAODL (product name, produced by Arkray, Inc.) that acts specifically on a peptide whose E-position was glycated (lysine peptide) were used in combination.

TABLE 16

| (First reagent: R1-9) | |
|---|---|
| FPOX-CE | 1.5 KU/L |
| POD | 10 KU/L |
| PIPES | 30 mmol/L (pH 7) |
| n-dodecyl-αβ-D-maltoside | 2.5 g/L |

| (Second reagent: R2-9) | |
|---|---|
| Metalloprotease (produced by Arkray, Inc.) | 4000 KU/L |
| CaCl$_2$ | 5 mmol/L |
| Tris | 200 mmol/L |
| MES | 30 mmol/L (pH 5.5) |
| Chromogenic reagent | 0.03 mmol/L |
| (Product name: DA-67, produced by Wako Pure Chemical Industries, Ltd.) | |

| (Third reagent: R3-9) | |
|---|---|
| FAODL | 20 KU/L |
| PIPES | 20 mmol/L (pH 7) |

(Sample)

Whole blood of a normal subject was diluted 31-fold with a below-described diluent and products listed below were diluted 31-fold with the diluent, thereby preparing samples. As a control for the samples, purified water was used.

IFCC control Barcelona, Low HbA1c, Normal Hemoglobin (HbA1c value (%)=3.2%)

IFCC control Barcelona, Medium HbA1c, Medium Hemoglobin (HbA1c value (%)=5.1%)

IFCC control Barcelona, High HbA1c, Normal Hemoglobin (HbA1c value (%)=7.5%)

| (Diluent) | |
|---|---|
| PIPES | 30 mmol/L (pH 7) |
| n-dodecyl-β-D-maltoside | 0.5 g/L |
| KNO$_2$ | 3 mM |

(Method)

6.5 μL of the respective samples and 6.5 μL of the purified water were mixed, and further, 78 μL of the respective first reagents (R1-9) were mixed therein. After these mixture solutions were incubated at 37° C. for 5 minutes, 19.5 µL of the second reagent (R2-9) was added thereto, which were subjected to the protease treatment at 37° C. for 4 minutes and effected first-step chromogenic reactions. After this reaction, 19.5 µL of the third reagent (R3-9) further was added, and second-step chromogenic reactions were effected (37° C., 6 minutes). Then, absorbance ($A_0$) at a wavelength of 658 nm of reaction liquids immediately before adding the second reagent, absorbance (A4) at the wavelength of 658 nm of the reaction liquids 4 minutes after the adding of the second reagent (immediately before adding the third reagent), and absorbance ($A_{10}$) at the wavelength of 658 nm of the reaction liquids 6 minutes after the adding of the third reagent were measured by a biochemical automatic analyzer (product name: JCA-BM8, produced by JEOL Ltd.), and differences thereof ($A_{4-A0}$) and ($A_{10}-A_4$) were obtained.

Results will be shown in Table 17 below. In the below Table 17, the absorbance difference of ($A_4-A_0$) corresponds to the HbA1c and the absorbance ($A_0-A_4$) corresponds to the GHbLys. Numerals in brackets represent differences from the result obtained by using the sample control (purified water).

TABLE 17

| | | Absorbance (Abs.) | | | |
|---|---|---|---|---|---|
| Example 9-1 | Purified water | Whole blood of normal subject | IFCC Low 3.2% | IFCC Medium 5.1% | IFCC High 7.5% |
| First reagent FPOX-CE ($A_4$-$A_0$) | 0.061 | 0.073 (0.012) | 0.072 (0.011) | 0.082 (0.021) | 0.095 (0.034) |
| Second reagent FAODL ($A_{10}$-$A_4$) | 0.039 | 0.042 (0.010) | 0.041 (0.008) | 0.048 (0.017) | 0.055 (0.030) |

As described above, the FPOX-CE reacts with the β-chain N-terminal peptide, and the FAODL reacts with the ε-position glycated lysine peptide, but it is known that the FAODL does not react with the β-chain N-terminal peptide. Thus, the β-chain N-terminal peptide and the ε-position glycated lysine peptide are obtained from the Hb by the cleavage by the protease treatment in the presence of n-dodecyl-β-D-maltoside, but they can be assayed continuously by using the two kinds of FAODs that have different substrate specificities. Then, it can be confirmed that, from the results shown in Table 17, the absorbance after the respective FAPD treatment was increased according to the increase of the HbA1c values (%) of the respective samples. Consequently, the method of the present example enables to assay the glycation degrees of the two kinds continuously.

INDUSTRIAL APPLICABILITY

As described above, according to the protein cleavage method of the present invention, for example, the β-chain N-terminal peptide or the like that is the feature of the HbA1c can be released by cleavage swiftly, so that a glycation amount of the protein can be determined precisely. Thus, the protein cleavage method and the method for assaying a glycation amount of the present invention are significantly useful in the fields of clinical examinations and the like.

The invention claimed is:

1. A protein cleavage method for cleaving a protein to obtain an amino acid or a peptide by a protease, wherein the protein is subjected to protease treatment in the presence of a compound represented by Formula (I) below, $$R\text{---}X \tag{I}$$

where, R represents straight-chain alkyl or straight-chain acyl with a carbon number of 9 to 16, branched-chain alkyl or branched-chain acyl with a carbon number of 10 to 40 and a main-chain carbon number of 9 to 16, or straight-chain alkyl with a straight-chain carbon number of 4 to 13 that is substituted by cycloalkyl with a carbon number of 3 to 8, and X represents a sugar residue wherein the protein is subjected to the protease treatment in the presence of the compound and a nitro compound.

2. The cleavage method according to claim 1, wherein, in the Formula (I), X represents a sugar residue of a monosaccharide or a disaccharide.

3. The cleavage method according to claim 2, wherein, in the Formula (I), X represents at least one sugar residue selected from the group consisting of mannoside, maltoside, fructopyranosyl-glucopyranoside and thiomaltoside.

4. The cleavage method according to claim 1, wherein the compound is at least one compound selected from the group consisting of 6-cyclohexylhexyl-β-D-maltoside, sucrose monolaurate, n-decyl-β-D-maltoside, n-dodecyl-β-D-maltoside, n-nonyl-β-D-thiomaltoside, hexadecy-β-D-maltoside, 5-cyclohexylpenthyl-β-D-maltoside, undecyl-β-D-maltoside, 3-oxatridecyl-α-D-mannoside and dodecyl-αβ-D-maltoside.

5. The cleavage method according to claim 1, wherein the protein is hemoglobin.

6. The cleavage method according to claim 1, wherein the amino acid cleaved from hemoglobin is at least one selected from the group consisting of a β-chain N-terminal valine, a lysine, glycated products of a β-chain N-terminal valine and a lysine, and
the peptide obtained by the cleavage from the hemoglobin is at least one selected from the group consisting of a peptide containing a β-chain N-terminal valine, a peptide containing a β-chain N-terminal glycated valine, a peptide containing a lysine, and a peptide containing a glycated lysine.

7. The cleavage method according to claim 1, wherein the peptide obtained by the cleavage from the protein is a peptide with a number of amino acid residues of 2 to 6.

8. The cleavage method according to claim 1, wherein the nitro compound is nitrous acid or a salt of nitrous acid.

9. A method for assaying a protein glycation degree comprising:
a step of cleaving a protein by a protease;
a step of allowing a fructosyl amino acid oxidase to act on a glycated part of the obtained protein cleavage product; and
a step of measuring a redox reaction between the glycated part and the fructosyl amino acid oxidase so as to determine the protein glycation degree,
wherein the protein is cleaved by the cleavage method according to claim 1, and the fructosyl amino acid oxidase is allowed to act on a glycated part of an amino acid or a peptide that is obtained by the cleavage step.

10. The assay method according to claim 9, wherein the nitro compound is nitrous acid or a salt of nitrous acid.

11. The assay method according to claim 9, wherein the protein is hemoglobin.

12. The assay method according to claim 11, wherein a glycation degree of the hemoglobin is a HbA1c value.

13. The assay method according to claim 12, wherein the protein cleavage product is a β-chain N-terminal valine or a peptide containing a β-chain N-terminal valine, and allows a fructosyl amino acid oxidase to act on the glycated part of the β-chain N-terminal valine.

14. The assay method according to claim 11, wherein a glycation degree of the hemoglobin is a lysine glycation degree.

15. The assay method according to claim 14, wherein the protein cleavage product is a lysine or a peptide containing a lysine, and allows a fructosyl amino acid oxidase to act on the glycated part of the lysine.

16. The assay method according to claim 11 which is a method for assaying a glycation degree of hemoglobin contained in a sample, wherein the sample is a whole blood sample, a blood cell sample or a hemolyzed sample of the whole blood sample or the blood cell sample.

17. The assay method according to claim 11, wherein
the compound represented by the Formula (I) is added to a sample containing the hemoglobin in advance of cleaving the hemoglobin by the protease,
an optical change amount of the sample to which the compound is added is measured so as to calculate an amount of the hemoglobin in the sample from this optical change amount,
on the other hand, the hemoglobin in the sample to which the compound is added is cleaved by the protease,
a redox reaction between a glycated part of the cleavage product and a fructosyl amino acid oxidase is measeured so as to measure a glycation amount of the hemoglobin, and a glycation degree of Hb is obtained from the amount of the hemoglobin and the glycation amount.

* * * * *